United States Patent [19]  [11] 4,151,835
Showell et al.  [45] May 1, 1979

[54] FOETAL SCALP ELECTRODES

[76] Inventors: Donald W. D. Showell, Britten St., Redditch, Worcs.; John Copeland, 451 Skellingthorpe Rd., Lincoln, both of England

[21] Appl. No.: 884,970

[22] Filed: Mar. 8, 1978

[51] Int. Cl.² ............................................. A61B 5/04
[52] U.S. Cl. ................................................. 128/642
[58] Field of Search ............. 128/2 B, 2.06 E, 2.1 E, 128/215, 418, DIG. 4, 419 P, 404, 335.5

[56] References Cited

U.S. PATENT DOCUMENTS

| | | | |
|---|---|---|---|
| 2,197,717 | 4/1940 | Bradshaw | 128/335.5 |
| 2,712,314 | 7/1955 | Kohl | 128/215 |
| 3,769,984 | 11/1973 | Muench | 128/404 |

FOREIGN PATENT DOCUMENTS 1316072  5/1973  United Kingdom ............... 128/2.06 E

OTHER PUBLICATIONS

Medtronic, Inc. Publication #TC68101r, Dec. 1968, pp. 1–21.

Primary Examiner—William E. Kamm
Attorney, Agent, or Firm—Lowe, King, Price & Becker

[57] ABSTRACT

A foetal scalp electrode of simple construction, which is simple to operate, and which affords secure attachment to the foetal scalp, has a tubular torsional spring member encircling an electrically conductive wire between an electrical connector and an insulated head member, whereby relative rotation of the connector and head member respectively manually against the torsion and oppositely upon release of the connector causes an arcuate contact needle on one end of the wire to move respectively into and out of the head member, the head member being provided with a concave surface facing oppositely to a flat surface from which the needle is normally urged by the torsion, so that the head member can be held securely in one hand close to a foetal scalp with a finger resting in the concave surface, which is preferably formed with ribs extending transversely with respect to the axis of the tubular torsional spring member, so as to improve the grip afforded by a finger engaging the concave surface still further by deterring sliding of the finger along the head member away from the connector.

15 Claims, 6 Drawing Figures

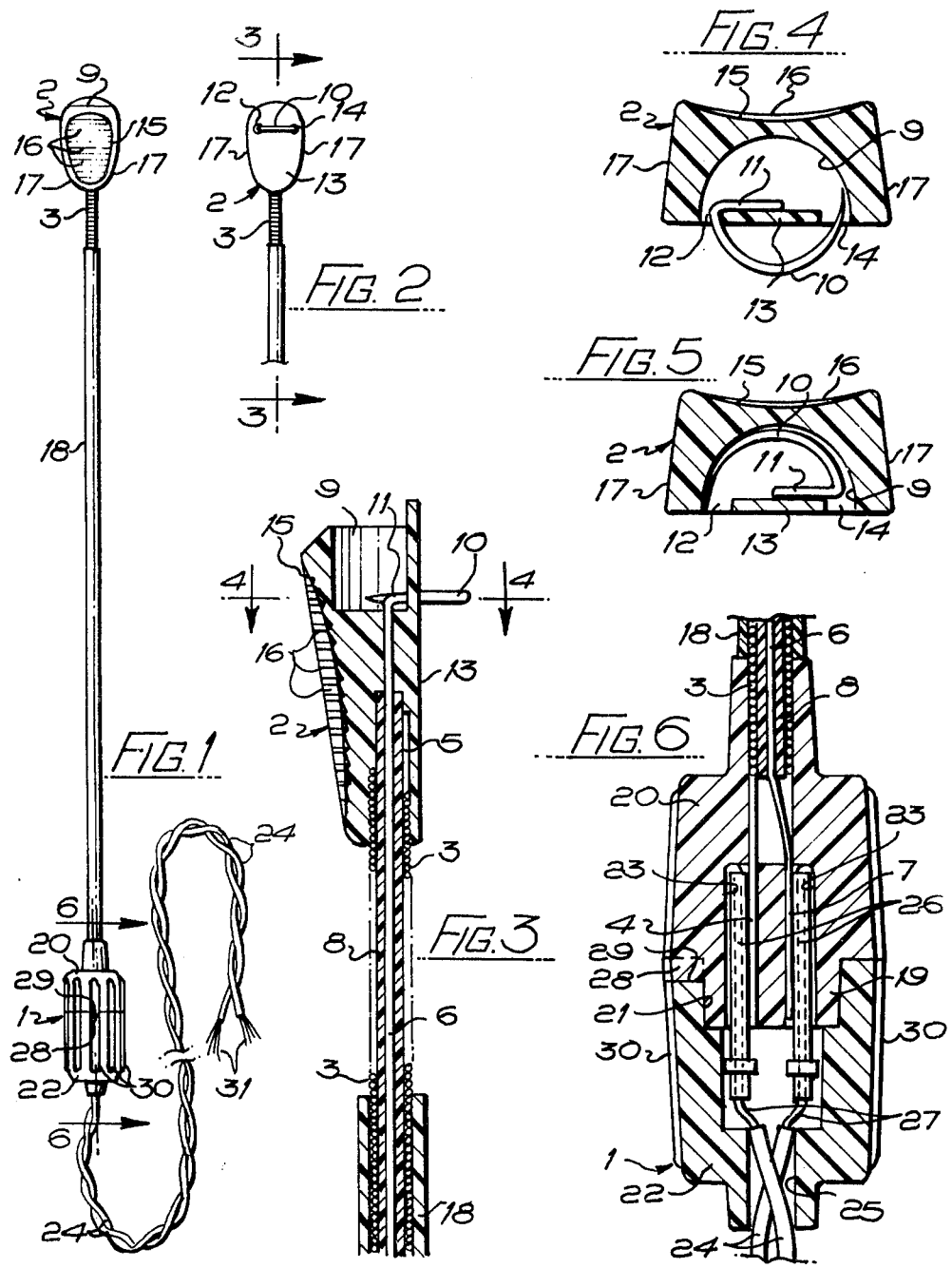

FOETAL SCALP ELECTRODES

This invention relates to foetal scalp electrodes and has for its object the provision of a foetal scalp electrode of simple construction, simple to operate, and affording secure attachment to the foetal scalp.

According to the present invention, a foetal scalp electrode comprises an electrical connector, a head member of electrically insulating material, a tubular torsional spring member secured at one end to the electrical connector, and secured at the other end to the head member, a central electrically conductive wire extending through the tubular torsional spring member from a terminal in the electrical connector to a cavity in the head member where the wire is provided with an electrically conductive arcuate needle on an electrically conductive arm extending radially from the wire, with the arcuate needle normally urged, by torsion in the tubular spring member, through a hole between the cavity and a flat surface on the outside of the head member, and with the point of the needle looping back to the flat surface, the outside of the head member also being provided with a concave surface facing oppositely to the flat surface.

With the head member of the electrode held, by one hand with a finger resting in the concave surface, in close proximity to the foetal scalp, the electrical connector is rotated, by the other hand, with respect to the head member, in opposition to the torsion in the tubular spring member, whereby the arcuate needle is withdrawn through the hole into the cavity in the head member, the head member then having its flat surface held against the foetal scalp by pressing with the finger resting in the concave surface, and the electrical connector returned relative to the head member, whereby the arcuate needle is forced back out through the hole and through the foetal scalp, the looping of the point of the needle back to the head member of the electrode and the torsion applied by the tubular spring member ensuring secure attachment of the electrode to the foetal scalp. Then, with the electrical connector connected to monitoring equipment, and the mother also connected to the monitoring equipment, the wire carries the signal picked up by the needle hooked in the foetal scalp.

The improved grip afforded by the concave surface on the head member, especially if the adjacent fingers engage the sides of the head member, may be further improved by forming the concave surface with ribs extending transversely with respect to the axis of the tubular torsional spring member, as such ribs deter the finger engaged therewith from sliding along the head member in a direction away from the electrical connector.

To release the electrode from the foetal scalp, the head member is held and the electrical connector is rotated with respect to the head member in opposition to the torsion in the tubular spring member, whereby the arcuate needle is withdrawn from the foetal scalp and into the cavity, and the head member is moved away from the foetal scalp before being released for the arcuate needle to spring back to its position partly outside the head member.

A second hole is preferably provided between the cavity and the flat surface of the head member for the point of the needle to enter when in said normal position looping back to the head member, to afford greater secureness when in use and shielding of the point when not in use.

The tubular torsional spring member may be an outer electrically conductive wire in the form of a helical spring with a terminal at one end in the electrical connector and with an insulating sheath (e.g. of polytetrafluoroethylene, so as to afford self-lubrication) inside the helical spring to insulate it from the central wire. The helical spring serves both to make electrical contact with the mother and as a screen for the central signal-carrying wire. The helical spring is preferably covered with insulating material over most of its length, to prevent abrasion, the exposed portion of the helical spring preferably being adjacent the head member.

Alternatively, the tubular torsional spring member may be a tube of plastic material, e.g., nylon, bonded to (or into) the electrical connector and the head member, serving also as insulation for the central wire, and an outer electrically conductive wire is preferably provided outside the tube, with a terminal at one end in the electrical connector and secured at the other end in the head member, to provide for contact of the outer wire with the mother.

The connector preferably comprises a two-part body of electrically insulating material with a plug and socket coupling, with a pair of axial holes in one of the body parts (conveniently the one with the plug) for passage of the central and outer wires, which are electrically joined to insulated leads passing through an axial hole in the other body part by means of pins pressed into the holes with the central and outer wires before fitting and sealing together of the body parts. The pins are preferably gold-plated, so as to ensure excellent electrical joints, and the pins may be tubular, to enable bared ends of the leads to be led through them and bent back before insertion into the holes with the central and outer wires.

The entire foetal scalp electrode is preferably enclosed in a sterile package, e.g., a double plastic envelope which is then sterilised. Alternatively, the entire electrode may be enclosed in a rigid plastic tubular container with an integral closed end and a plug sealed to the other end, and which is then sterilised, the plug being hollow and accommodating the connector, which therefore can be grasped after the seal is broken and the plug removed from the container, without risk of contamination of the hand grasping the connector by contact with the outside of the container. The electrode is, however, disposable or reusable.

An embodiment of the invention will now be described, by way of example only, with reference to the accompanying drawings, in which:

FIG. 1 is a general view of a foetal scalp electrode in accordance with the invention;

FIG. 2 is a fragmentary elevation showing the other side of the head member of the electrode of FIG. 1;

FIG. 3 is an enlarged fragmentary section taken from the line 3—3 of FIG. 2;

FIG. 4 is a section on the line 4—4 of FIG. 3;

FIG. 5 corresponds to FIG. 4 but shows the arcuate needle of the electrode withdrawn into the head member; and FIG. 6 is an enlarged fragmentary section taken from the line 6—6 of FIG. 1.

The foetal scalp electrode shown in the drawings comprises an electrical connector 1, a head member 2 of electrically insulating material (e.g. nylon), an outer electrically conductive wire in the form of a helical spring 3, with a terminal 4 in the electrical connector constituted by a straightened end portion of the spring, and with another straightened end 5 secured to the head member, and a central electrically conductive wire 6 with a terminal 7 at one end in the electrical connector, the central wire extending through an insulating sheath 8 (e.g. of polytetrafluoroethylene, so as to be self-lubricating) inside the helical spring 3, and the other end of the wire being in a cavity 9 in the head member and provided with an electrically conductive arcuate needle 10 on an electrically conductive arm 11 radial to the wire 6, with the arcuate needle normally urged, by torsion in the helical spring, through a hole 12 between the cavity and a flat surface 13 on the outside of the head member 2, and with the point of the needle looping back into the head member through a second hole 14 provided between the cavity 9 and the flat surface 13 for the point of the needle to enter, to afford greater secureness when in use (as will be described presently) and shielding of the point when not in use.

The outside of the head member 2 is also provided with a concave surface 15 facing oppositely to the flat surface 13, and the concave surface is formed with ribs 16 extending transversely with respect to the axis of the helical spring 3, which ribs deter a finger engaged therewith from sliding along the head member in a direction away from the electrical connector 1 when the adjacent fingers engage the sides 17 of the head member.

The helical spring 3 is covered with insulating material 18 over most of its length, to prevent abrasion, the exposed portion of the helical spring, for making contact with the mother, being adjacent the head member 2.

The connector 1, (see FIG. 6) comprises a two-part body of electrically insulating material (e.g. nylon), with a plug 19 on one body part 20 and a socket 21 in the other body part 22 for coupling the body parts together, and with a pair of axial holes 23 in the body part 20 for passage of the central and outer wire terminals 7 and 4, which are electrically joined to insulated leads 24 passing through an axial hole 25 in the body part 22 by means of pins 26 pressed into the holes 23 before fitting and sealing together of the body parts. The pins 26 are preferably gold-plated, so as to ensure excellent electrical joints, and the pins are tubular, to enable bared ends 27 of the leads 24 to be led through them and bent back before insertion into the holes containing the central and outer wires. Relative rotation of the body parts 20, 22 is prevented, whilst sealing of them together is being effected, by means of a projection 28 on the body part 20 engaged with a notch 29 in the body part 22. Ribs 30 extending longitudinally of the body parts of the connector 1 assist in gaining a good grip. The other ends 31 of the leads 24 are bared, to enable the electrical connector 1 to be connected to monitoring equipment (not shown).

With the head member 2 of the electrode held, by one hand with a finger resting in the concave surface 15 with the ribs 16 and the adjacent fingers gripping the sides 17, in close proximity to the foetal scalp, the electrical connector 1 is rotated, by the other hand, with respect to the head member, in opposition to the torsion in the helical spring 3, whereby the arcuate needle 10 is withdrawn through the hole 12 into the cavity in the head member, which then has its flat surface 13 held against the foetal scalp by pressing with the finger resting in the concave surface 15, and the electrical connector 1 returned relative to the head member 2, whereby the arcuate needle 10 is forced back out through the hole 12 and through the foetal scalp, the looping of the point of the needle 10 back to the head member and through the hole 14, and the torsion applied by the helical spring 3, ensuring secure attachment of the electrode to the foetal scalp.

To release the electrode from the foetal scalp, the head member 2 is held (as before) and the electrical connector 1 is rotated with respect to the head member in opposition to the torsion in the helical spring 3, whereby the arcuate needle 10 is withdrawn from the foetal scalp and into the cavity 9, and the head member is moved away from the foetal scalp before being released for the arcuate needle to spring back to its position partly outside the head member.

What we claim is:

1. A foetal scalp electrode comprising an electrical connector, a head member of electrically insulating material having a flat surface thereon and a cavity formed therein, said head member including a hole formed in its flat surface extending into said cavity, a tubular torsional spring member secured at one to the electrical connector and secured at the other end to the head member, a central electrically conductive wire extending through the tubular torsional spring member, one end of said wire providing a terminal in the electrical connector and its opposite end having an electrically conductive arm extending radially therefrom into said cavity in said head member, an electrically conductive arcuate needle formed on said electrically conductive arm and having a point extending outwardly from said head member through said hole, said arcuate needle being normally urged, by torsion in the tubular spring member, through said hole with the point of the needle looping back to said flat surface, said head member also being provided with the concave outer surface facing oppositely to the flat surface.

2. A foetal scalp electrode as in claim 1, wherein the concave surface is formed with ribs extending transversely with respect to the axis of the tubular torsional spring member.

3. A foetal scalp electrode as in claim 1 wherein a second hole is provided between the cavity and the flat surface of the head member for the point of the needle to enter when in said normal position looping back to the head member.

4. A foetal scalp electrode as in claim 1, wherein the tubular torsional spring member is an outer electrically conductive wire in the form of a helical spring with a terminal at one end in the electrical connector and with an insulating sheath inside the helical spring to insulate it from the central wire.

5. A foetal scalp electrode as in claim 4, wherein the insulating sheath is formed of polytetrafluoroethylene.

6. A foetal scalp electrode as in claim 4, wherein the helical spring includes insulating material covering said spring over most of its length.

7. A foetal scalp electrode as in claim 6, wherein said helical spring includes an exposed portion adjacent the head member.

8. A foetal scalp electrode as in claim 4, wherein the connector comprises a two-part body of electrically insulating material with a plug and socket coupling, with a pair of axial holes in one of the body parts for passage of the central and outer wires, which are electrically joined to insulated leads passing through an axial hole in the other body part by means of pins pressed into the holes with the central and outer wires before fitting and sealing together of the body parts.

9. A foetal scalp electrode as in claim 8, wherein the pair of axial holes are provided in the body part with the plug.

10. A foetal scalp electrode as in claim 8, wherein the pins are gold-plated.

11. A foetal scalp electrode as in claim 8, wherein the pins are tubular, and the bared ends of the leads are led through them and bent back before insertion into the holes with the central and outer wires.

12. A foetal scalp electrode as in claim 1, wherein the tubular torsional spring member is a tube of plastic material bonded to the electrical connector and the head member.

13. A foetal scalp electrode as in claim 12, wherein the plastic material is nylon.

14. A foetal scalp electrode as in claim 12, wherein an outer electrically conductive wire is provided outside the tube, with a terminal at one end in the electrical connector and secured at the other end in the head member.

15. A foetal scalp electrode as in claim 1, wherein said head member is tapered from said cavity toward said tubular spring member along the thickness between said concave outer surface and said flat surface.

* * * * *